United States Patent [19]

Lüthy

[11] Patent Number: 5,482,920
[45] Date of Patent: Jan. 9, 1996

[54] TRIAZINYL COMPOUNDS WITH HERBICIDAL ACTIVITY

[75] Inventor: Christoph Lüthy, Münchenstein, Switzerland

[73] Assignee: Ciba-Geigy Corporation, Tarrytown, N.Y.

[21] Appl. No.: 193,198

[22] PCT Filed: Jun. 3, 1993

[86] PCT No.: PCT/EP93/01393

§ 371 Date: Feb. 15, 1994

§ 102(e) Date: Feb. 15, 1994

[87] PCT Pub. No.: WO93/25540

PCT Pub. Date: Dec. 22, 1993

[30] Foreign Application Priority Data

Jun. 17, 1992 [CH] Switzerland ............................ 1907/92

[51] Int. Cl.[6] ..................... C07D 251/46; C07D 251/30; C07D 403/12; A01N 43/66
[52] U.S. Cl. .......................... 504/227; 540/362; 540/363; 540/454; 540/524; 544/60; 544/195; 544/214; 544/113; 544/211; 544/212; 544/213; 544/194; 544/218; 544/219; 504/196; 504/197; 504/219; 504/221; 504/225; 504/230; 504/231
[58] Field of Search ...................... 504/230, 231, 504/196, 221; 544/211, 212, 194, 218, 219, 213, 60, 195, 214, 113; 540/362, 524

[56] References Cited

FOREIGN PATENT DOCUMENTS

| | | |
|---|---|---|
| 0347811 | 12/1989 | European Pat. Off. . |
| 0400741 | 12/1990 | European Pat. Off. . |
| 0409368 | 1/1991 | European Pat. Off. . |
| 0409369 | 1/1991 | European Pat. Off. . |
| 0481512 | 4/1992 | European Pat. Off. . |
| 0517215 | 12/1992 | European Pat. Off. . |
| 0541041 | 5/1993 | European Pat. Off. . |

OTHER PUBLICATIONS

Chem. Abst. 116:59390u, p. 865, 1992, Wada et al.

*Primary Examiner*—John M. Ford
*Attorney, Agent, or Firm*—Marla J. Mathias; George R. Dohmann

[57] ABSTRACT

Pyrimidinyloxy- and triazinyloxy- and pyrimidinylthio- and triazinylthio-butyric acid derivatives of formula I

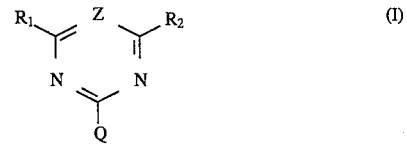
(I)

wherein
Q is

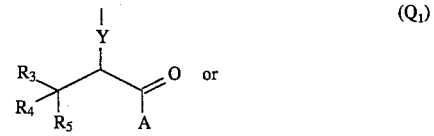
($Q_1$)

or

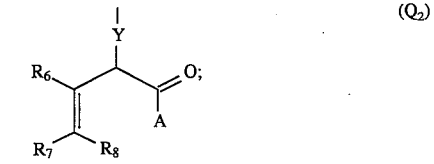
($Q_2$);

A is hydroxy or a group

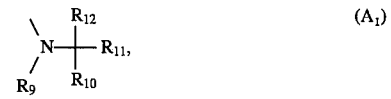
($A_1$)

($A_2$)

($A_3$) or ($A_4$)

and the other substituents are as described in patent claim 1, and salts of compounds of formula I, have herbicidal action and are suitable as active ingredients in weed control compositions.

18 Claims, No Drawings

TRIAZINYL COMPOUNDS WITH HERBICIDAL ACTIVITY

This application is a 371 of PCT/EP93/01393 filed Jun. 3, 1993.

The present invention relates to novel, herbicidally active pyrimidinyl-oxy- and triazinyl-oxy- and -thio-propionic acid derivatives, to processes for the preparation thereof, to compositions comprising them as active ingredients, and to the use thereof in controlling weeds, especially selectively in crops of useful plants.

Pyrimidinyl-oxy- and triazinyl-oxy- and -thio-acetic acid derivatives having herbicidal action are generally known. Such compounds are described, for example, in European Patent Applications Nos. 0 347 811, 0 400 741, 0 409 368, 0 481 512 and 0 517 215. Novel herbicidally active pyrimidinyl-oxy- and triazinyl-oxy- and -thio-propionic acid derivatives have now been found.

The pyrimidinyloxy- and triazinyloxy- and pyrimidinylthio- and triazinylthio-propionic acid derivatives according to the invention have the formula I

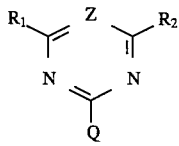

(I)

wherein

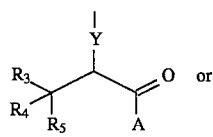

(Q₁)

or

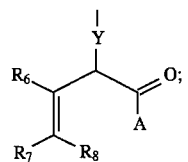

(Q₂)

A is a group

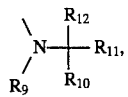

(A₁)

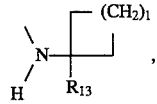

(A₂)

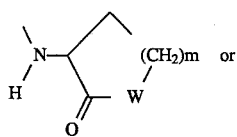

(A₃)

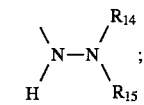

(A₄)

Y is oxygen or sulfur;
Z is methine or nitrogen;

$R_1$ is methyl, ethyl, cyclopropyl, methoxy, ethoxy, difluoromethoxy, methylthio, ethylthio, methylamino, ethylamino, dimethylamino or diethylamino;

$R_2$ is methyl, fluorine, chlorine, methoxy, ethoxy or difluoromethoxy;

$R_3$ is hydrogen, $C_{1-6}$alkyl, $C_{3-6}$cycloalkyl, $C_{1-6}$allcyl mono-substituted by chlorine or mono- to hexa-substituted by fluorine; phenyl, thienyl, or phenyl or thienyl mono- or di-substituted by fluorine, chlorine, methyl or by methoxy;

$R_4$ is hydrogen, $C_{1-3}$alkyl or, together with $R_3$, $-(CH_2)_n-$;

$R_5$ is hydrogen, methyl, fluorine, chlorine, bromine, $C_{1-6}$alkoxy, $C_{3-6}$alkenyloxy, $C_{3-6}$-alkynyloxy, $C_{3-4}$cycloalkyl-$C_{1-2}$alkoxy, $C_{4-6}$cycloalkoxy, $C_{1-4}$alkoxy mono-substituted by cyano, phenyl, $C_{1-2}$alkoxy or chlorine or mono- to hexa-substituted by fluorine; $C_{1-6}$alkylthio or cyano;

$R_6$ is hydrogen, $C_{1-6}$alkyl, phenyl or, together with $R_7$, $-(CH_2)_p-$, $-CH=CH-CH=CH-$, $-N-CH-CH=CH-$ or $-S-CH=CH-$;

$R_7$ is hydrogen or methyl;

$R_8$ is hydrogen or methyl;

$R_9$ is hydrogen, methyl or, together with $R_{11}$, $-(CH_2)_q-$, $-CH_2CH(OH)CH_2-$, $-CH_2SCH_2-$ or $-CH_2CH_2SCH_2-$;

$R_{10}$ and $R_{13}$ are each independently of the other hydroxymethyl, formyl, cyano, phosphono, phosphino, methylphosphino or a group COX, $R_{11}$ is hydrogen, $C_{1-4}$alkyl, trifluoromethyl, or $C_{1-4}$-alkyl substituted by hydroxy, $C_{1-4}$-alkoxy, mercapto, $C_{1-4}$alkylmercapto, vinyl, phenyl, 4-hydroxyphenyl, 4-imidazolyl, 3-indolyl, carboxy, $C_{1-4}$alkoxycarbonyl, 2-propenyloxycarbonyl, cyano, carbamoyl, methylphosphino or by methylsulfoximino; ethynyl, vinyl, phenyl, or vinyl or phenyl substituted by chlorine, methyl or by methoxy;

$R_{12}$ is hydrogen or methyl;

$R_{14}$ is hydrogen, methyl or, together with $R_{15}$, a 5- or 6-membered heterocyclic ring which may in turn contain a nitrogen atom, an oxygen atom, a sulfur atom or a group $-S(O)-$, $-S(O)_2-$, $-C(O)-$, $-C(O)O-$, $-C(O)S-$ $-C(S)O-$ or $-C(S)S-$ and/or may additionally be mono- or poly-substituted by $C_{1-6}$alkyl or mono-substituted by benzyl, $C_{1-3}$alkoxy, hydroxy-$C_{1-2}$alkyl or by $C_{1-2}$alkoxy-$C_{1-2}$alkyl;

$R_{15}$ is hydrogen, $C_{1-6}$alkyl, phenyl, or phenyl mono- or di-substituted by fluorine, chlorine, bromine, iodine, $C_{1-4}$alkyl, trifluoromethyl, $C_{1-3}$alkoxy, difluoroalkoxy, cyano, nitro or by $C_{1-4}$alkoxycarbonyl; pyridyl, or pyridyl mono- or di-substituted by fluorine, chlorine, methyl, methoxy or by trifluoromethyl;

l is 0, 1, 2 or 3;
m is 0, 1, 2 or 3;
n is 2, 3, 4 or 5;
p is 3 or 4;
q is 2 or 3;
W is oxygen, sulfur, NH or $-NH-O-$;
X is hydroxy, $C_{1-4}$alkoxy, $C_{3-4}$alkenyloxy, benzyloxy, amino, $C_{1-4}$alkylamino, $C_{2-4}$-dialkylamino or a group

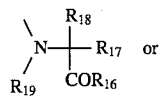 (X₁)

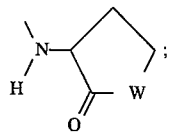 (X₂)

R₁₆ is hydroxy, C₁₋₄alkoxy, 2-propenyloxy, benzyloxy, amino or a further amino acid group (X₁);

R₁₇ is hydrogen, C₁₋₄alkyl or benzyl;

R₁₈ is hydrogen or methyl;

R₁₉ is hydrogen or, together with R₁₇, —(CH₂)₃—; and the salts of those compounds of formula I having a free carboxy group; with the proviso that Y is sulfur when R₁ and R₂ are methoxy, Q is Q₁, R₃ and R₄ are methyl, R₅ is hydrogen, A is the group A₄, and R₁₄ and R₁₅ are simultaneously either hydrogen or methyl; with the exception of the compounds N-β-[2-(4,6-dimethoxy-pyrimidin-2-yl)oxy] -3-methyl-butyryl]-dimethylhydrazide and N-[2-(4,6-dimethoxy-pyrimidin-2-yl)oxy] -3-methyl-butyryl]-hydrazide.

If the compounds of formula I contain an asymmetric centre, the compounds may occur in optically isomeric forms. Some of the compounds of formula I may occur in mutomeric forms (for example keto-enol tautomerism). If an aliphatic C=C double bond is present it is also possible for geometrical isomerism (E form or Z form) to occur. This applies especially to those compounds of formula I wherein Q is Q₂. Formula I therefore includes all possible stereoisomers that occur in the form of enantiomers, mutomers, diastereoisomers, E/Z isomers or mixtures thereof.

In formula I the alkyl, alkenyl and alkynyl radicals may be straight-chain or branched. The same applies also to the or each alkyl moiety of alkoxy-, alkylthio- and alkoxycarbonyl-containing (corresponding to C₁₋₄carboxy-containing) groups and of other alkyl-containing groups.

In the definitions, C₁₋₆alkyl is, for example, methyl, ethyl, n-propyl, isopropyl, n-butyl, sec-butyl, isobutyl, tert-butyl, pentyl and the pentyl isomers, hexyl and the hexyl isomers. C₂₋₆Alkenyl and C₂₋₆alkynyl radicals occurring in the substituents may also be straight-chain or branched, for example vinyl, allyl, methallyl, 1-methylvinyl, but-2-en-1-yl, 2-propyn-1-yl, 1-methyl-2-propyn-1-yl and 2-butyn-1-yl. Halomethyl is, for example, chloromethyl, fluoromethyl or trifluoromethyl.

Alkoxycarbonyl is, for example: methoxycarbonyl, ethoxycarbonyl, n-propoxycarbonyl, isopropoxycarbonyl, n-butoxycarbonyl and tert-butoxycarbonyl, preferably methoxycarbonyl, ethoxycarbonyl and tert-butoxycarbonyl.

The groupings (A₁), (A₂) and (A₃) will be understood as being especially the following substituents T:

T1: 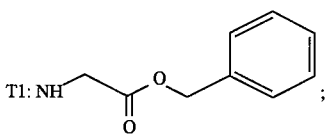

-continued

T2: 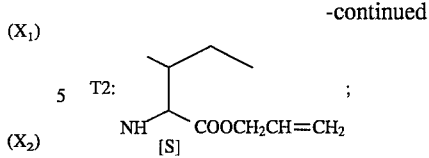

T3: 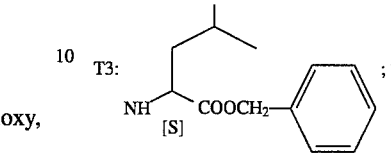

T4: 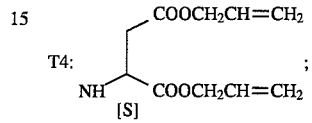

T5: 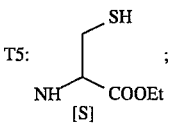

T6: 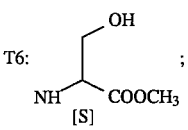

T7: 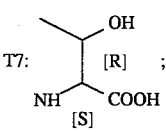

T8: 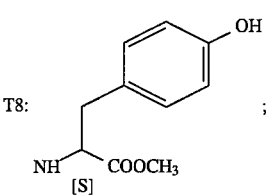

T9: 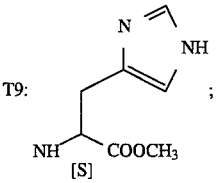

T10: 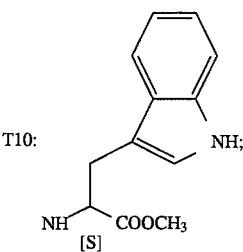

-continued
T11: 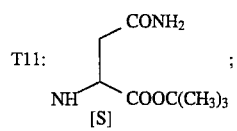
T12: 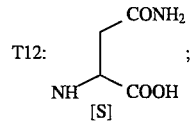
T13: 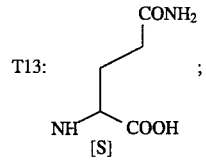
T14: 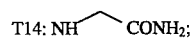
T15: 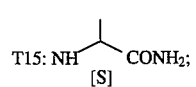
T16: 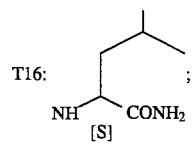
T17: 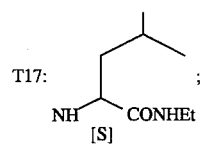
T18: 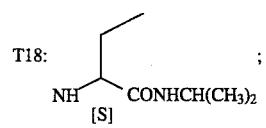
T19: 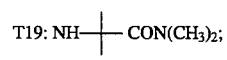
T20: 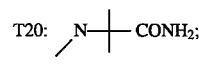
T21: 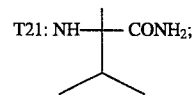
T22: 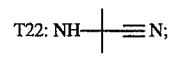
T23: 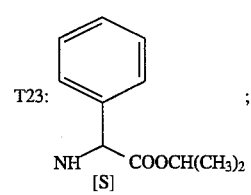
T24: 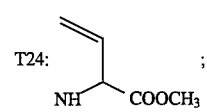
-continued
T25: 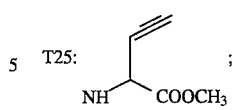
T26: 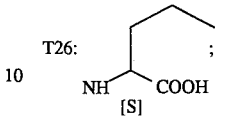
T27: 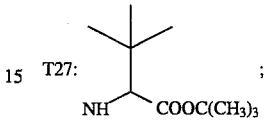
T28: 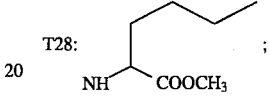
T29: 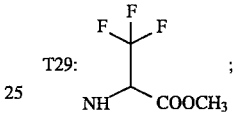
T30: 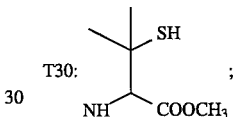
T31: 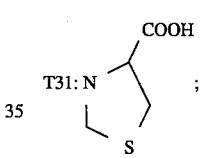
T32: 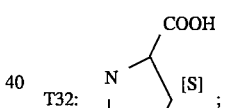
T33: 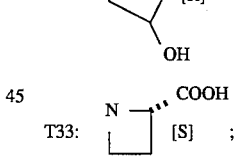
T34: 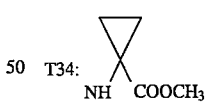
T35: 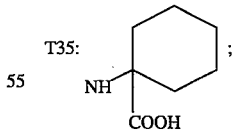
T36: 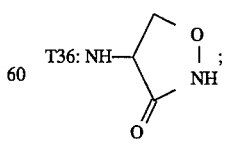

-continued

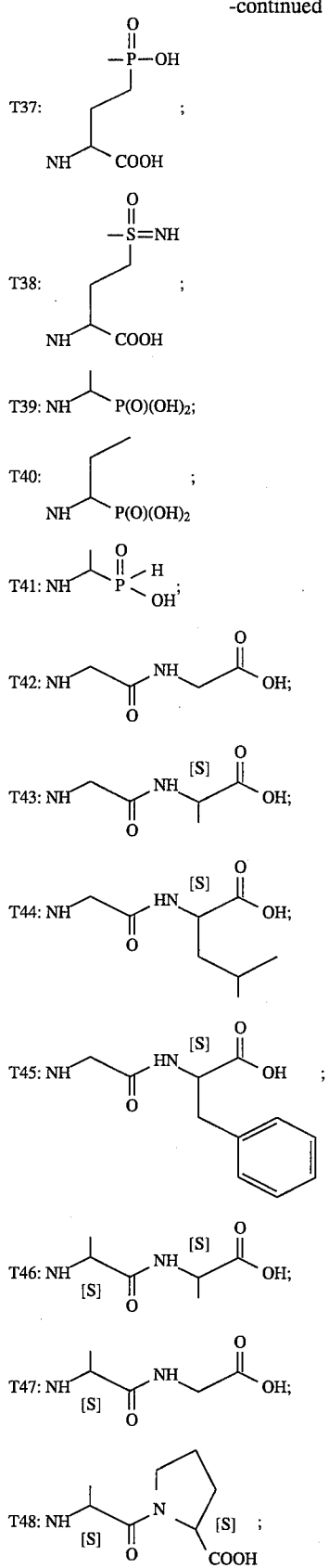

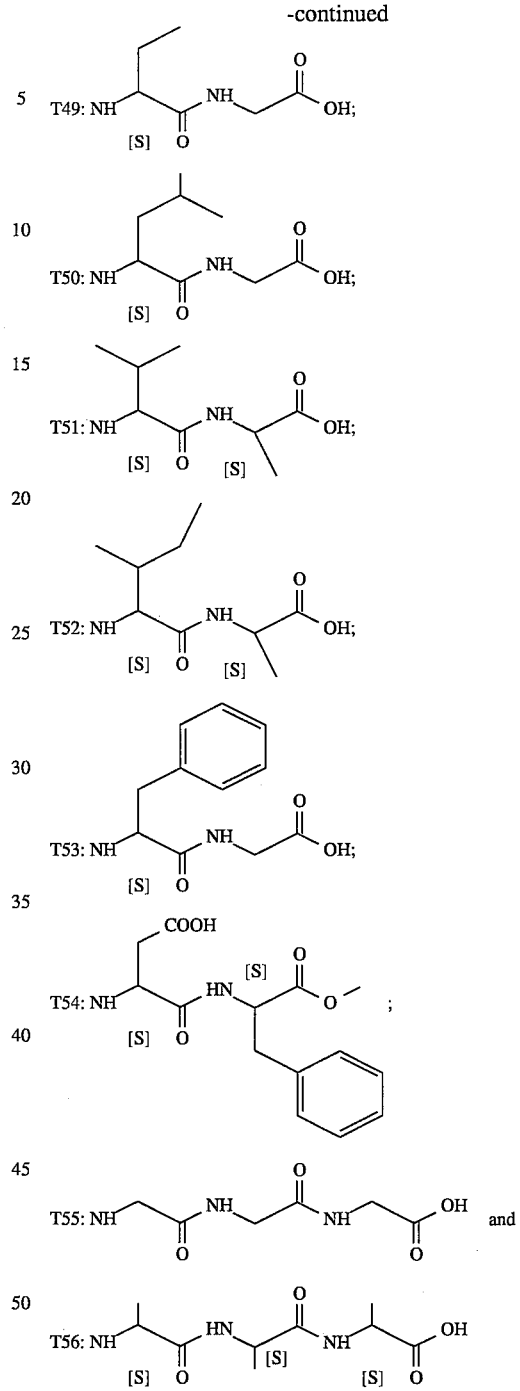

Suitable salts of free carboxy groups are especially alkali metal salts, such as lithium, sodium, potassium, alkaline earth metal salts, such as magnesium, calcium, or salts of organic ammonium bases, such as ammonia, primary, secondary or tertiary alkylamines, for example methylammonium, diethylammonium, triethylammonium, morpholinium or pyridinium.

Preference is given to those compounds of formula I wherein $R_3$ is hydrogen, $C_{1-6}$alkyl, $C_{3-6}$cycloalkyl, $C_{1-6}$alkyl monosubstituted by chlorine or mono- to hexa-substituted by fluorine; phenyl, thienyl, or phenyl mono- or di-substituted by fluorine, chlorine, methyl or by methoxy;

$R_4$ is hydrogen, methyl or, together with $R_3$, —$(CH_2)_n$—;

$R_5$ is hydrogen, methyl, fluorine, chlorine, bromine, $C_{1-6}$alkoxy, $C_{3-6}$alkenyloxy, $C_{3-6}$alkynyloxy, $C_{3-4}$cycloalkyl-$C_{1-2}$alkoxy, $C_{1-6}$cycloalkoxy, $C_{1-4}$alkoxy mono-substituted by cyano, $C_{1-2}$alkoxy or chlorine or mono- to hexa-substituted by fluorine; $C_{1-6}$alkylthio or cyano, and $R_6$ is hydrogen, $C_{1-4}$alkyl, phenyl or, together with $R_7$, —$(CH_2)_p$—, —CH—CH—CH=CH—, —N—CH—CH=CH— or —S—CH=CH—.

Preference is further given to those compounds of formula I wherein $R_1$ is methyl, dimethylamino or methoxy; and $R_2$ is methyl, methoxy, ethoxy or difluoromethoxy.

In very especially preferred compounds of formula I, $R_1$ and $R_2$ are methoxy.

In addition, special preference is given to those compounds of formula I wherein Q is a group

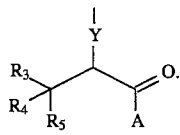
(Q₁)

Special emphasis should be given to those compounds of formula I wherein a) Z is methine;

b) Q is a group

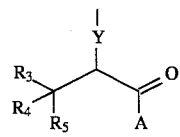
(Q₁)

wherein $R_3$ is preferably $C_{1-3}$alkyl or phenyl, $R_4$ is methyl or, together with $R_3$, —$(CH_2)_4$—, and $R_5$ is hydrogen, fluorine, methyl, cyano or $C_{1-4}$alkoxy; those compounds of formula I wherein Z is roethine, $R_1$ is methoxy and $R_2$ is methoxy are especially preferred.

In a preferred sub-group of compounds of formula I, A is a group

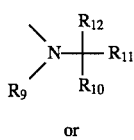
(A₁)

or

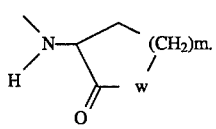
(A₃)

Of that group, special preference is given to those compounds of formula I wherein c) A is an <S>-chiral group

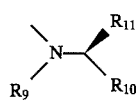
(A₁')

or

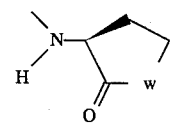
(A₃')

wherein $R_9$ is hydrogen or, together with $R_{11}$, —$(CH_2)_3$—, $R_1$ is a group COX wherein X is as defined for formula I, $R_{11}$ is hydrogen or $C_{1-4}$alkyl and W is oxygen or sulfur; those compounds of formula I wherein Z is methine, $R_1$ is methoxy and $R_2$ is methoxy are especially preferred.

A further prominent group comprises those compounds of formula I wherein

A is

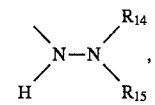
(A₄)

and preferably d) $R_{14}$ is hydrogen or methyl and $R_{15}$ is $C_{1-4}$alkyl, phenyl, or phenyl mono- or di-substituted by fluorine, chlorine, methyl, trifluoromethyl, methoxy or by nitro; pyridyl or pyrazinyl; or pyridyl or pyrazinyl mono- or di-substituted by fluorine, chlorine, methyl or by trifluoromethyl; or $R_{14}$ and $R_{15}$ together with the nitrogen atom to which they are bonded form a 5- or 6-membered heterocyclic ring which may in turn contain a nitrogen atom, an oxygen atom or a group —C(O)O— and/or may additionally be mono- or di-substituted by methyl or mono-substituted by methoxymethyl; those compounds of formula I wherein Z is methine, $R_1$ is methoxy and $R_2$ is methoxy are especially preferred.

Of the compounds of group d), special emphasis should be given to those wherein $R_{14}$ is hydrogen, and $R_{15}$ is tert-butyl, phenyl, or phenyl mono- or di-substituted by fluorine, chlorine, methyl, trifluoromethyl, methoxy or by nitro; pyridyl or pyrazinyl; or pyridyl or pyrazinyl mono- or di-substituted by fluorine, chlorine, methyl or by trifluoromethyl; or $R_{14}$ and $R_{15}$ together with the nitrogen atom to which they are bonded form a 5- or 6-membered heterocyclic ring which may in turn contain a nitrogen atom, an oxygen atom or a group —C(O)O— and/or may additionally be mono- or di-substituted by methyl or mono-substituted by methoxymethyl.

Special emphasis should also be given to those compounds of formula I wherein Y is oxygen.

The following especially preferred individual compounds falling within the scope of formula I may be mentioned:

N-[2-[(4,6-dimethoxy-pyrimidin-2-yl)oxy]-3-methyl-butyryl]-L-alanine ethyl ester, N-[2-[(4,6-dimethoxy-pyrimidin-2-yl)oxy]-3-methyl-butyryl]-L-glutamine diethyl ester, N-[2-[(4,6-dimethoxy-pyrimidin-2-yl)thio]-3-methyl-butyryl]-glycine, N-[2-[(4,6-dimethoxy-pyrimidin-2-yl)thio]-3-methyl-butyryl]-L-alanine, N-[2-[(4,6-dimethoxy-pyrimidin-2-yl)thio]-3-methyl-butyryl]-L-methylalanine tert-butyl ester, N-[2-[(4,6-dimethoxy-pyrim din-2-yl)thio]-3-methyl-butyryl]-L-methylalanine, N-[2-[(4,6-dimethoxy-pyrimidin-2-yl)oxy]-3-methyl-butyryl]-L-isoleucine, N-[2-[(4,6-dimethoxy-pyrimidin-2-yl)oxy]-3-methyl-butyryl]-L-proline, N-[2-[(4,6-dimethoxy-pyrimidin-2-yl)oxy]-3-methyl-butyryl]-L-methylalanine tert-butyl ester, N-[2-[(4,6-dimethoxy-pyrimidin-2-yl)oxy]-3-methyl-butyryl]-L-methylalanine, N-[2-[(4,6-dimethoxy-pyrimidin-2-yl)oxy]-3-methyl-butyryl]-L-alanine tert-butyl ester, N-[2-[(4,6-dimethoxy-pyrimidin-2-yl)oxy]-3-methyl-butyryl]-L-alanine, N-[2-[(4,6-dimethoxy-pyrimidin-2-yl)oxy]-3-methyl-butyryl]-L-homoserine lactone, N-$\beta$-[2-[(4,6-dimethoxypyrimidin-2-yl)thio]-3-methyl-butyryl]-o-tolylhydrazide, N-[2-[(4,6-dimethoxy-pyrimidin-2-yl)thio]-3-methyl-butyryl]-L-valine, N-[2-[(4,6-dimethoxy-pyrimidin-2-yl)thio]-3-methyl-butyryl]-L-isoleucine, and N-[2-[(4,6-dimethoxy-pyrimidin-2-yl)oxy]-3-methyl-butyryl]-L-alanine ethyl ester.

Compounds of formula Ia wherein $R_1$, $R_2$, $R_3$, $R_4$, $R_5$, A, Y and Z are as defined for formula I can be prepared by reacting a compound of formula IIa" or an anhydride of formula IIa'''

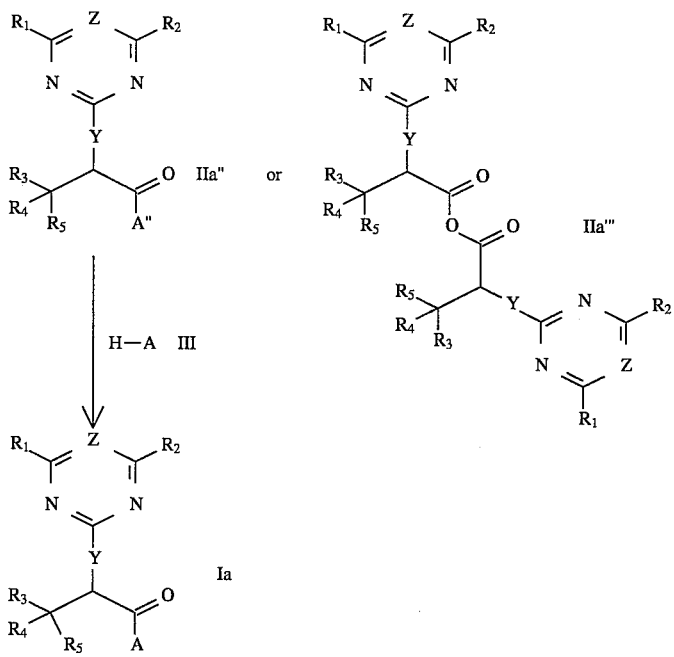

wherein $R_1$, $R_2$, $R_3$, $R_4$, $R_5$, Y and Z are as defined above and wherein A" is a leaving group, such as chlorine, fluorine, bromine, 2,4,6-triisopropylsulfonyl, imidazolyl, triazolyl, 2-thiono-thiazolidin-3-yl or N,N'-dicyclohexyl-isoureidyl, with a nucleophilic compound of formula III wherein A is a group $A_1$, $A_2$, $A_3$ or $A_4$, with $A_1$, $A_2$, $A_3$ and $A_4$ being as defined for formula I, optionally in the presence of a base and a solvent.

That reaction is advantageously carried out in the presence of a base as acid-binding agent. Suitable bases are especially tertiary amines, for example triethylamine, N,N-dimethylaniline, 1,8-diazabicyclo[5.4.0]undec-7-ene, imidazole, pyridine or 2,5-dimethylpyridine. They can be used in catalytic amounts, as well as in stoichiometric amounts or in excess, preferably in stoichiometric amounts or up to a slight excess. It is also possible to use as base a slight excess of the starting material of formula III used.

The reaction is preferably carried out also in the presence of a suitable solvent or diluent. Suitable diluents are: hydrocarbons, for example toluene; halogenated hydrocarbons, for example dichloromethane, 1,2-dichloroethane or chlorobenzene; ethers, for example diethyl ether, diethoxymethane or tert-butyl methyl ether; aprotic solvents, for example acetonitrile; protic solvents, for example ethanol or water; or two-phase systems, for example a mixture of dichloromethane/water, toluene/water or tert-butyl methyl ether/water.

The reaction temperatures may be varied within a wide range from approximately $-40°$ C. up to the boiling temperature of the solvent used. The reaction is, however, preferably carried out at a temperature of from approximately $-20°$ to approximately $+30°$ C., especially at approximately from $-10°$ to $+10°$. The reaction times may vary greatly, however, depending upon the temperature of the reaction mixture and the base used.

Compounds of formula IIa wherein A" is chlorine or bromine can be prepared, for example, by reacting an acid of formula IIa'

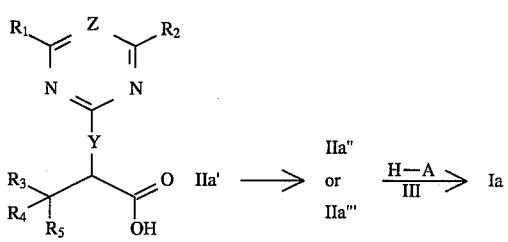

wherein $R_1$, $R_2$, $R_3$, $R_4$, $R_5$, Y and Z are as defined above and wherein A is hydroxy, with a chlorinating agent, such as phosphorus oxychloride, thionyl chloride, oxalyl chloride or phosgene, phosphorus pentachloride, phosphorus oxybromide, especially phosphorus oxychloride, in the presence of a base, for example triethylamine, dimethylaniline or pyridine, and optionally in a solvent, such as a hydrocarbon, for example toluene, a halogenated hydrocarbon, for example methylene chloride, or an ether, for example tetrahydrofuran, in a temperature range of from −20° C. up to the reflux temperature of the reaction mixture, preferably from −5° C. to room temperature.

If desired, it is also possible to react the corresponding acid chloride (A" is chlorine ) or imidazolide (A" is imidazole), also without isolation, with the corresponding nucleophilic compound of formula III, optionally in the presence of an additional base, for example triethylamine. That reaction is likewise effected in a temperature range of approximately from −20° C. up to the reflux temperature of the solvent used, preferably from −5° C. to room temperature.

Alternatively, an acid of formula IIa' may advantageously first be converted using from 0.50 to 0.55 equivalents of phosphorus oxychloride and a slight excess of from 2.0 to 3.0 equivalents of triethylamine into the corresponding more stable acid anhydride of formula IIa''' which is then reacted with the corresponding nucleophilic compound of formula III.

Compounds of formula IIa" wherein A" is 2,4,6-triisopropylsulfonyl, imidazolyl, triazolyl, 2-thiono-thiazolidin-3-yl or N,N'-dicyclohexyl-isoureidyl can be prepared, likewise from compounds of formula IIa, in accordance with known conversion processes using 1-(2,4,6-triisopropylphenylsulfonyl)-imidazole (Y. A. Berlin et. al., Tetrahedron letters 1973, 1353), 1-(2,4,6-triisopropylphenylsulfonyl)-1H-1,2,4-triazole (N. Katagiri, et. al., Chem. Commun. 1974, 325), 1,1'-carbonyl-diimidazole, 1,1'-carbonyl-di( 1,2,4)-triazole) (H. A. Staab, Angew. Chem. 74, 407 (1962)), thiazolylidin-2-thione (Y. Nagao et. al. Tetrahedron letters, 21, 841 (1980)) or dicyclohexylcarbodiimide. In those processes it is likewise unnecessary to isolate the intermediate of formula IIa" in order to convert it "in situ" as described above using a nucleophilic compound of formula 1H into a compound of formula In.

In an analogous manner it is also possible to prepare the compounds of formula Ib wherein $R_1$, $R_2$, $R_6$, $R_7$, $R_8$, A, Y and Z are as defined above, by reacting a compound of formula IIb" or a corresponding anhydride of formula IIb'''

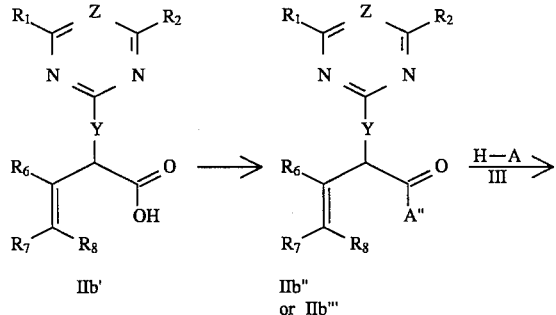

IIb'    IIb"
        or IIb'''

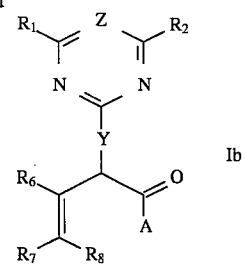

Ib wherein $R_1$, $R_2$, $R_6$, $R_7$, $R_8$, Y and Z are as defined above and wherein A" is one of the above-mentioned leaving groups, with a nucleophilic compound of formula III wherein A is a group $A_1$, $A_2$, $A_3$ or $A_4$, with $A_1$, $A_2$, $A_3$ and $A_4$ being as defined for formula I, optionally in the presence of a base and a solvent. Suitable bases and suitable solvents include those already mentioned above.

Compounds of formula Ia and Ib wherein X in the group COX represented by $R_{10}$ and $R_{13}$ is amino, $C_{1-4}$alkylamino, $C_{2-4}$dialkylamino or a further group

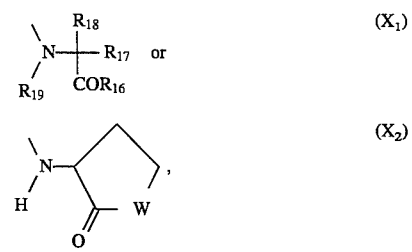

can also be prepared, for example, in accordance with the conversion reactions known to the person skilled in the art from peptide chemistry, from compounds of formula I wherein X in the group COX is hydroxy, tert-butoxy, 2-propenyloxy or benzyloxy.

Compounds of formulae IIa' and IIb' wherein $R_1$, $R_2$, $R_3$, $R_4$, $R_6$, $R_7$, $R_8$, Y and Z are as defined above and compounds of formula III are either known (IIa' for example from European Patent Applications Nos. 0 347 811, 0 400 741, 0 409 368, 0 481 512 and 0 517 215) or can be prepared according to known processes.

Compounds of formula IIb' wherein $R_1$, $R_2$, $R_7$, $R_8$, Y and Z are as defined above and $R_6$ is $C_{1-6}$alkyl or, together with $R_7$, —$(CH_2)_p$—, can be prepared by deprotonation of a compound of formula IV

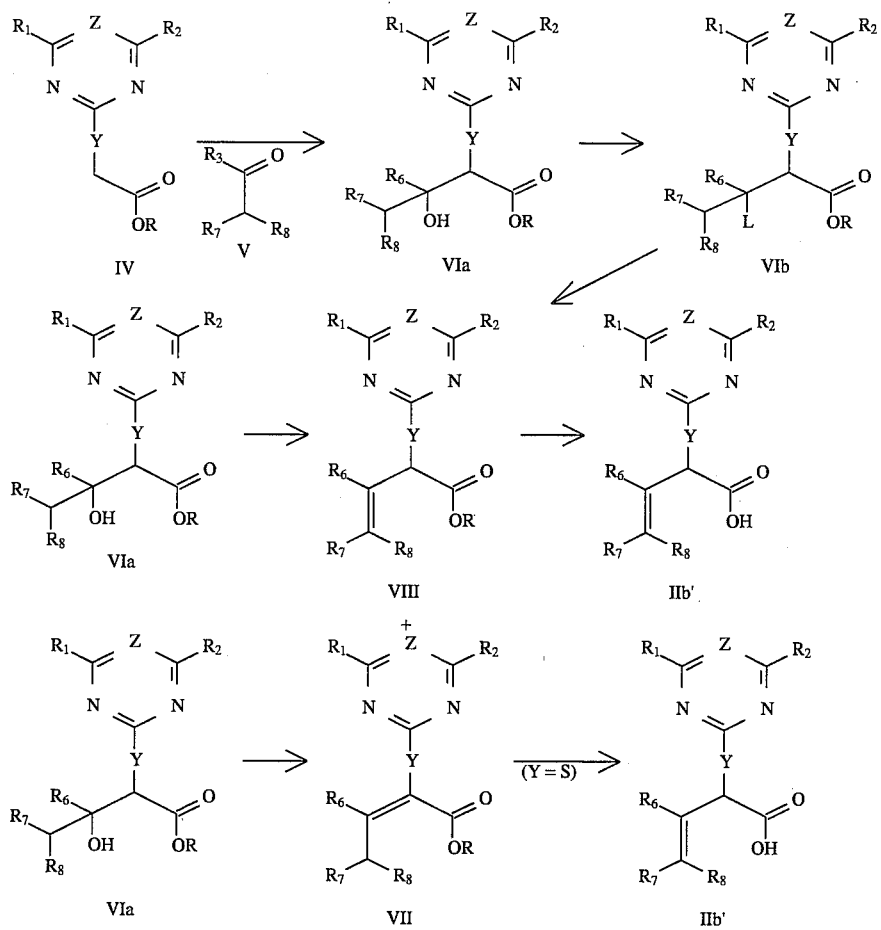

wherein $R_1$, $R_2$ and Z are as defined above and OR is $C_{1-4}$alkoxy, 2-propenyloxy or benzyloxy, but especially tert-butoxy, with a suitable base, for example lithium diisopropylamide, n-butyllithium, sec-butyllithium, phenyllithium or lithium hexamethyldisilazane, under the reaction conditions familiar to the person skilled in the art at. temperatures of approximately from −78° to −40° C. in a solvent, for example tetrahydrofuran, and reaction with a corresponding aldehyde or ketone of formula V to form a compound of formula VIa which is then converted via a compound of formula VIb, VII or VIII into a compound of formula IIb'.

Compounds of formula VIa, VIb or VIII or, especially when Y is sulfur, a compound of formula VII can be converted into the compounds of formula IIb' under suitable hydrolysing and alehydrating conditions, for example by treatment of a compound of formula VIII wherein OR is tert-butoxy with trifluoroacetic acid or, when OR is benzyloxy, by reaction hydrogenolytically with hydrogen in the presence of a palladium/carbon catalyst or, when OR is 2-propenyloxy, by reaction with tris-triphenylphosphine-rhodium(I) chloride and water.

For the conversion of the compound of formula VIa into a compound of formula VII or VIII there are suitable organic bases, for example triethylamine, dimethylaminopyridine or 1,8-diazabicyclo[5.4.0]undec-7-ene, or inorganic bases, for example sodium hydride, sodium hydroxide or potassium carbonate. The rearrangement of compounds of formula VII to form the compounds of formula VIII is advantageously effected in a diluent, for example toluene, acetonitrile, tetrahydrofuran, dichloromethane, ethanol, water, acetic acid or a mixture thereof, for example methanol and water. It is also advantageous for the dehydration to convert the compound of formula Vh into a compound of formula VIb having a suitable leaving group L, for example a mesylate or tosylate group or a halogen group, especially a chlorine group, by esterification of the hydroxy compound of formula VIa or the lithium salt thereof directly in the presence of a sulfonic acid chloride, or indirectly, optionally in the presence of a base, for example triethylamine or dimethylaminopyridine, and subsequent dehydration with heating, or by treatment with a chlorinating agent, for example thionyl chloride, and subsequent treatment with a base mentioned above.

Some of the compounds of formula VII and VIII are known (for example from European Patent Applications Nos. 0 409 369 and 0 347 811) or they can be prepared analogously to known processes.

The compounds of formula I are generally used successfully at rates of application of from 0.001 to 2 kg/ha, especially from 0.005 to 1 kg/ha. The concentration required to achieve the desired effect can be determined by experiment. It is dependent on the type of action, the stage of development of the cultivated plant and of the weed, and also on the application (place, time, method) and, in dependence on those parameters, can vary within wide limits.

The compounds of formula I are distinguished by growth-inhibiting and herbicidal properties, which render them excellently suitable for use in crops of useful plants, especially in cereals, cotton, soybeans, rape, sugar beet, maize and rice.

The invention relates also to herbicidal and plant growth regulating compositions comprising a novel compound of formula I, and to methods of inhibiting plant growth.

The active ingredients present in the compositions according to the invention influence plant growth in different ways depending on the time of application, the concentration, the type of application and the environmental conditions. Plant growth regulators of formula I can, for example, inhibit the vegetative growth of plants. This type of action is valuable in the case of lawn areas, in the cultivation of ornamentals, in fruit plantations, in the case of roadside embankments and in sports fields and industrial sites, and also in the specific inhibition of side-shoots, as in the case of tobacco. In agriculture, inhibition of the vegetative growth of cereals leads, owing to strengthening of the stalk, to reduced lodging, and a similar agronomic effect is achieved in rape, sunflowers, maize and other cultivated plants. Moreover, by inhibiting the vegetative growth it is possible to increase the number of plants per unit area. Another field of application of growth inhibitors is the selective control of cover plants in plantations or widely spaced crops by greatly inhibiting the growth of the cover crops without killing them, so that competition with the main crop is eliminated but the agronomically positive effects, such as erosion prevention, fixing of nitrogen and loose soil structure, are preserved.

A method of inhibiting plant growth is to be understood as being a method of controlling a plant's natural development without changing its life-cycle, as determined by genetic characteristics, in the sense of mutation. The method of regulating growth is applied at a time in the plants development that has to be determined for each individual case. The compounds of formula I can be applied pre- or post-emergence, for example to the seeds or seedlings, to roots, tubers, stalks, leaves, blossoms or other parts of the plant. This can be done, for example, by applying the compound as such or in the form of a composition to the plants, and/or by treating the plant's nutrient medium (soil).

Various methods and techniques are suitable for the use of the compounds of formula I or of compositions comprising them for regulating plant growth, for example the following:

i) Seed dressing a) Dressing the seeds with an active ingredient formulated as a wettable powder, by shaking in a container until the formulation is uniformly distributed over the surface of the seeds (dry dressing). Up to 4 g of a compound of formula I (in the case of a 50% formulation: up to 8.0 g of wettable powder) are used per 1 kg of seed.

b) Dressing the seeds with an emulsifiable concentrate of the active ingredient or with an aqueous solution of the compound of formula I formulated as a wettable powder according to method a) (wet dressing).

c) Dressing by soaking the seeds for a period of from 1 to 72 hours in a liquor comprising up to 1000 ppm of a compound of formula I and, if desired, subsequently drying the seeds (seed soaking).

Seed dressing or treatment of the germinated seedling are naturally the preferred methods of application because the treatment with the active ingredient is then directed wholly at the target crop. From 0.001 g to 4.0 g of active ingredient are normally used per 1 kg of seed, although, depending on the method employed, which also allows the addition of other active ingredients or micronutrients, amounts that exceed or fall short of the specified concentration limits may be employed (repeat dressing).

ii) Controlled release of active ingredient

A solution of the active ingredient is applied to mineral granule carriers or polymerised granules (urea/formaldehyde) and allowed to dry. If required, a coating may be applied (coated granules), which allows the active ingredient to be released in metered amounts over a specific period of time.

The compounds of formula I are used in unmodified form, as obtainable from the synthesis, or, preferably, together with the adjuvants customarily employed in formulation technology and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying; atomising, dusting, wetting, scattering or pouring, are chosen in accordance with the intended objectives and the prevailing circumstances.

The formulations, i.e. the compositions, preparations or mixtures comprising the compound (active ingredient) of formula I and, where appropriate, one or more solid or liquid adjuvants, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons, such as paraffins, cyclohexane or tetrahydronaphthalene; alcohols, such as ethanol, propanol or butanol; glycols and their ethers and esters, such as propylene glycol or dipropylene glycol ether; ketones, such as cyclohexanone, isophorone or diacetone alcohol; strongly polar solvents, such as N-methyl-2-pyrrolidone, dimethyl sulfoxide or water; vegetable oils and esters thereof, such as rape oil, castor off or soybean oil; and, where appropriate, also silicone oils.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues.

Depending upon the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described inter alia in the following publications:

"Mc Cutcheon's Detergents and Emulsifiers Annual", Mc Publishing Corp., Glen Rock, N.J., 1988.

M. and J. Ash, "Encyclopedia of Surfactants", Vol. I–III, Chemical Publishing Co., New York, 1980–1981.

Dr. Helmut Stache "Tensid-Taschenbuch" (Surfactant Handbook), Carl Hanser Verlag, Munich/Vienna 1981.

The herbicidal compositions usually comprise 0.1 to 99%, preferably 0.1 to 95%, of a compound of formula I, 1 to 99% of a solid or liquid adjuvant, and 0 to 25%, preferably 0.1 to 25%, of a surfactant.

Whereas commercial products will preferably be formulated as concentrates, the end user will normally employ dilute formulations.

The compositions may also comprise further auxiliaries, such as stabilisers, e.g. vegetable oils or epoxidised vegetable oils (epoxidised coconut oil, rape oil or soybean oil), antifoams, e.g. silicone oil, preservatives, viscosity regulators, binders and tackifiers, as well as fertilisers or other active ingredients for obtaining special effects.

Preferred formulations have especially the following composition (throughout, percentages are by weight):
Emulsifiable concentrates:
  active ingredient: 1 to 20%, preferably 5 to 10%
  surface-active agent: 5 to 30%, preferably 10 to 20%
  liquid carrier: 15 to 94%, preferably 70 to 85%
Dusts:
  active ingredient: 0.1 to 10%, preferably 0.1 to 1%
  solid carrier: 99.9 to 90%, preferably 99.9 to 99%
Suspension concentrates:
  active ingredient: 5 to 75%, preferably 10 to 50%
  water: 94 to 24%, preferably 88 to 30%
  surface-active agent: 1 to 40%, preferably 2 to 30%
Wettable powders:
  active ingredient: 0.5 to 90%, preferably 1 to 80%
  surface-active agent: 0.5 to 20%, preferably 1 to 15%
  solid carrier: 5 to 95%, preferably 15 to 90%
Granules:
  active ingredient: 0.5 to 30%, preferably 3 to 15%
  solid carrier: 99.5 to 70%, preferably 97 to 85%

PREPARATION EXAMPLES

The following Examples serve to illustrate the invention.

Example P1

Preparation of
N-β-[2-[(4,6-dimethoxy-pyrimidin-2-yl)thio]-3-methyl-butyryl] -o-tolylhydrazide (Example 1.101)

An initial batch of 2.0 g of 2-[(4,6-dimethoxy-pyrimidin-2-yl)thio]-3-methylbutyric acid together with 4.5 ml of triethylamine in 70 ml of diethoxymethane is prepared. At −5° C., 1.24 g of phosphorus oxychloride in 10 ml of diethoxymethane are added dropwise thereto in the course of one minute, and the reaction mixture is stirred for 15 minutes at −5° C. and then 2.3 g of o-tolylhydrazine hydrochloride are added. After being stirred for 15 minutes the reaction mixture is poured into ice-water and extracted twice with ethyl acetate. The organic phases are washed in succession with ice-cold, dilute sodium hydroxide solution, dilute hydrochloric acid and with saturated sodium chloride solution, dried over magnesium sulfate and concentrated by evaporation, and the product that remains behind is purified on silica gel, eluant ethyl acetate/hexane 1:3, yielding pure N-β-[2-[(4,6 -dimethoxy-pyrimidin-2-yl)thio]-3-methyl-butyryl]-o-tolylhydrazide in the form of yellowish crystals; m.p.: 111°–114° C.

Example P 2

Preparation of
N-[-2-[(4,6-dimethoxy-pyrimidin-2-yl)oxy]-3-methyl-butyryl]-L-alanine (Example 1.024)

2 g of N-[2-[(4,6-dimethoxy-pyrimidin-2-yl)oxy]-3-methyl-butyryl]-L-alanine tert-butyl ester (Example 1.023) are added to 20 ml of trifluoroacetic acid. After one hour, the reaction mixture is concentrated by evaporation, taken up in ethyl acetate, washed once with dilute hydrochloric acid, dried over sodium sulfate and again concentrated by evaporation, yielding N-[2-[(4,6-dimethoxy-pyrimidin-2-yl)oxy]-3-methyl-butyryl] -L-alanine as a crystalline product; m.p.: 157°–160° C. (from ethyl acetate).

Example P 3

Preparation of
2-[(4,6-dimethoxy-pyrimidin-2-yl)thio-3-methyl-3-pentenoic acid (Example 5.011) and
2-[(4,6-dimethoxy-pyrimidin-2-yl)thio]-3-ethyl-3-butenoic acid (Example 5.012)

At −50° C., 16.6 ml of a 1.6 molar n-butyllithium solution in hexane are introduced into a prepared mixture of 3.1 g of N,N,N',N'-tetramethylethylenediamine and 25 ml of absolute tetrahydrofuran. 6.2 g of 2-[(4,6-dimethoxy-pyrimidin-2-yl)thio]-acetic acid ethyl ester dissolved in 15 ml of tetrahydrofuran are then added dropwise thereto at a temperature of −65° C. and the mixture is stirred for 20 minutes. 2.4 ml of ethyl methyl ketone are added at a temperature below −60° C. and the reaction mixture is heated to room temperature in the course of 1 hour. Ice-water is then added to the reaction mixture which is then extracted twice with ethyl acetate, washed with saturated sodium chloride solution, dried and concentrated by evaporation. Column chromatography on silica gel, eluant ethyl acetate/hexane 1:4 yields pure 2-[(4,6-dimethoxy-pyrimidin-2-yl)thio]-3-hydroxy-3-methylpentanoic acid ethyl ester in the form of a yellow oil; $^1$H-NMR(CDCl$_3$): 1.36/1.40, 2s, CH$_3$; 3.17/3.31, OH; 3.93, s, OCH$_3$; 4.2, m, OC$\underline{H}_2$CH$_3$; 4.79/4.80, 2s, CH; 5.76, s, CH; 70/30 isomeric mixture.

2.0 g of that product are heated at reflux for 7 hours in the presence of 2.9 g of triethylamine, 3.4 g of dimethylaminopyridine and 3.2 g of methanesulfonic acid chloride in 12 ml of toluene, the reaction being monitored by gas chromatography. The mixture is then taken up in ethyl acetate and washed once each with dilute hydrochloric acid, dilute sodium hydrogen carbonate solution and sodium chloride solution. After being dried over magnesium sulfate the reaction mixture is concentrated by evaporation under reduced pressure. Chromatographic separation, eluant ethyl acetate/hexane 1:9, yields a), in the form of a 1:1 isomeric mixture, approximately 0.7 g of 2-[(4,6-dimethoxy-pyrimidin-2-yl)thio] -3-methyl-2-pentenoic acid ethyl ester; H-NMR(CDCl$_3$): 2.16/2.22, 2s, CH$_3$; 2.55/2.57, 2q, C$\underline{H}_2$CH$_3$; 3.88, s, OCH$_3$; 4.15, q, OC$\underline{H}_2$CH$_3$; 5.71, s, CH; and b), in the form of an isomeric mixture, approximately 0.6 g of 2-[(4,6-dimethoxy-pyrimidin-2-yl)thio] -3-methyl-3-pentenoic acid ethyl ester; H-NMR(CDCl$_3$): 1.66, d, J=7Hz, CH$_3$; 1.81, t, J=1Hz, CH$_3$; 3.90, s, OC$\underline{H}_3$; 4.2, m, OC$\underline{H}_2$CH$_3$; 5.00, b, CH; 5.72, s, CH; and 2-[(4,6 -dimethoxy-pyrimidin-2-yl)thio]-3-ethyl-3-butenoic acid ethyl ester; H-NMR(CDCl$_3$): H-NMR(CDCl$_3$): 2.28 m and 2.55, q, C$\underline{H}_3$; 3.89, s, OCH$_3$; 4.2, m, OC$\underline{H}_2$CH$_3$; 5.09, m, and 5.25, m, C=CH$_2$; 5.73, s, CH.

The 2-[(4,6-dimethoxy-pyrimidin-2-yl)thio]-3-methyl-2-pentenoic acid ethyl ester a) obtained above is heated at 60° C. for 3.5 hours in a solution of 0.75 g of potassium hydroxide in 20 ml of water/methanol 1:1. The reaction mixture is then poured into ice-water and separated from the neutral phase once with diethyl ether. The aqueous phase is acidified with 5N hydrochloric acid and extracted twice with ethyl acetate, dried over sodium sulfate and concentrated by evaporation. Purification by chromatography yields, as main component in the form of a colourless oil, a) 2-[(4,6-dimethoxy-pyrimidin-2-yl)thio] -3-methyl-3-pentenoic acid (Example 5.011); H-NMR(CDCl$_3$): 1.54/1.68, d, J=7Hz, CH$_3$; 1.84, m, CH$_3$; 3.89, s, OCH$_3$; 4.90, s, CH, 5.76, s, CH; and b) 2-[(4,6 -dimethoxy-pyrimidin-2-yl)thio]-3-ethyl-3-butenoic acid (Example 5.012); H-NMR(CDCl$_3$): 2.3 m, C$\underline{H}_2$CH$_3$; 3.89, s, OCH$_3$; 4.89, s, CH, 5.16, m, and 5.31, m, C=CH$_2$, 5.77, s, CH.

In an analogous manner it is also possible to prepare the compounds listed in Tables 1, 2, 6 and 7, and the intermediates given in Tables 4 and 5.

TABLE 1

Compounds of formula Ia

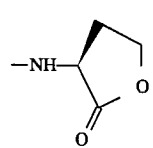

| Comp. No. | Y | R$^3$ | R$^4$ | A | m.p. [°C.]/ physical data |
|---|---|---|---|---|---|
| 1.001 | O | CH$_3$ | CH$_3$ | [Gly]—O-t-Bu | 147–149° |
| 1.002 | " | " | " | [Ala]—OEt | 85–88° |
| 1.003 | " | " | " | [Val]—O-t-Bu | 49–51° |
| 1.004 | " | " | " | [Ile]—O-t-Bu | Rf: 0.48 (EtOAc/ hexane 1:1) |
| 1.005 | " | " | " | [Leu]—O-t-Bu | 51–53° |
| 1.006 | " | " | " | [Glu]—(OEt)$_2$ | 80–83° |
| 1.007 | S | " | " | [Gly]—O-t-Bu | 150–151° |
| 1.008 | " | " | " | [Ala]—O-t-Bu | 52–56° |
| 1.009 | " | " | " | [Gly]—OH | 143–146° |
| 1.010 | " | " | " | [Ala]—OH | 156–157° |
| 1.011 | " | " | " | [Me—Ala]—O-t-Bu | Rf: 0.57 (EtOAC/ hexane 7:8) |
| 1.012 | " | " | " | [Me—Ala]—OH | 130–131° |
| 1.013 | " | " | " | [Val]—O-t-Bu | Rf: 0.59 (EtOAc/ hexane 7:8) |
| 1.014 | " | " | " | [Leu]—O-t-Bu | Rf: 0.61 (EtOAc/ hexane 7:8) |
| 1.015 | " | " | " | [Val]—OH | 147–149° |
| 1.016 | " | " | " | [Leu]—OH | 162–164° |
| 1.017 | " | " | " | [Ile]—O-t-Bu | Rf: 0.61 (EtOAc/ hexane 7:8) |
| 1.018 | " | " | " | [Pro]—O-t-Bu | Rf: 0.42 (EtOAc/ hexane 7:8) |
| 1.019 | " | " | " | [Ile]—OH | 143–145° |
| 1.020 | " | " | " | [Pro]—OH | Rf: 0.08 (EtOAc/ MeOH 3:1) |
| 1.021 | O | CH$_3$ | CH$_3$ | [Me—Ala]—O-t-Bu | 77–80° |
| 1.022 | " | " | " | [Me—Ala]—OH | 134–137° |
| 1.023 | " | " | " | [Ala]—O-t-Bu | 86–88° |
| 1.024 | " | " | " | [Ala]—OH | 157–160° |
| 1.025 | S | " | " | [Glu]—(OEt)$_2$ | Rf.: 0.43 (EtOAc/ hexane 1:1) |
| 1.026 | " | " | " | 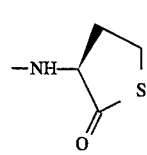 | 143–146° |
| 1.027 | " | " | " | | 164–167° |

TABLE 1-continued

Compounds of formula Ia

Ia: structure with CH3O, OCH3 on pyrimidine ring, N, N, Y, R3, R4, A, =O

| Comp. No. | Y | R³ | R⁴ | A | m.p. [°C.]/ physical data |
|---|---|---|---|---|---|
| 1.028 | O | " | " | -NH- (tetrahydrothiophene-2-one) | 194–198° |
| 1.029 | " | " | " | -NH- (γ-butyrolactone) | 176–180° |
| 1.030 | S | " | " | -NH- (cyclopentane carboxylate) | Rf.: 0.38 (EtOAc/hexane 7:8) |
| 1.031 | " | " | " | -N (thiomorpholine ethyl ester) | Rf.: 0.63 (EtOAc/hexane 2:1) |
| 1.032 | " | " | " | S- -NH- (methyl ester) | 123–126° |
| 1.101 | S | CH₃ | CH₃ | o-tolylhydrazinyl | 111–114° |
| 1.102 | " | " | " | o-chlorophenyl-hydrazinyl | |
| 1.103 | " | " | " | o-fluorophenyl-hydrazinyl | |
| 1.104 | " | " | " | phenylhydrazinyl | |
| 1.105 | " | " | " | p-fluorophenyl-hydrazinyl | |
| 1.106 | " | " | " | p-chlorophenyl-hydrazinyl | |
| 1.107 | " | " | " | p-methoxyphenyl-hydrazinyl | |
| 1.108 | " | " | " | p-nitrophenyl-hydrazinyl | |
| 1.109 | " | " | " | m-chlorophenyl-hydrazinyl | |
| 1.110 | " | " | " | m-trifluoromethyl-phenylhydrazinyl | |
| 1.111 | " | " | " | m-chloro-o-tolylhydrazinyl | |
| 1.112 | " | " | " | 2,4-difluorophenyl-hydrazinyl | |
| 1.113 | " | " | " | tert-butylhydrazinyl | |
| 1.114 | " | " | " | dimethylhydrazinyl | |
| 1.115 | " | " | " | -NH-N (oxazolidinone) | |
| 1.116 | " | " | " | -NH-N (pyrrolidinyl) | |
| 1.117 | " | " | " | -NH-N O (morpholinyl) | |
| 1.118 | O | CH₃ | CH₃ | o-tolylhydrazinyl | |
| 1.119 | " | " | " | o-chlorophenyl-hydrazinyl | |
| 1.120 | " | " | " | o-fluorophenyl-hydrazinyl | |
| 1.121 | " | " | " | phenylhydrazinyl | |
| 1.122 | " | " | " | p-fluorophenyl-hydrazinyl | |
| 1.123 | " | " | " | p-chlorophenyl-hydrazinyl | |
| 1.124 | " | " | " | p-methoxyphenyl-hydrazinyl | |
| 1.125 | " | " | " | p-nitrophenyl-hydrazinyl | |
| 1.126 | " | " | " | m-chlorophenyl-hydrazinyl | |
| 1.127 | " | " | " | m-trifluoromethyl-phenylhydrazinyl | |
| 1.128 | " | " | " | m-chloro-o-tolylhydrazinyl | |
| 1.129 | " | " | " | o-xylylhydrazinyl | |
| 1.130 | " | " | " | 2,4-difluorophenyl-hydrazinyl | |
| 1.131 | " | " | " | tert-butylhydrazinyl | |
| 1.132 | " | " | " | -NH-N (oxazolidinone) | |
| 1.133 | " | " | " | -NH-N (pyrrolidinyl) | |

TABLE 1-continued

Compounds of formula Ia

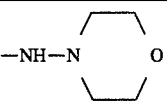

| Comp. No. | Y | R³ | R⁴ | A | m.p. [°C.]/ physical data |
|---|---|---|---|---|---|
| 1.134 | " | " | " | —NH—N⌐O⌐ | |
| 1.135 | O | CH₃ | C₂H₅ | [Ala]—OEt | |
| 1.136 | " | " | " | [Leu]—OEt | |
| 1.137 | " | " | " | [Asp]—(OEt)₂ | |
| 1.138 | S | " | " | [Ala]—OMe | |
| 1.139 | " | " | " | [Leu]—OMe | |
| 1.140 | " | " | " | [Asp]—(OMe)₂ | |
| 1.141 | O | " | " | phenylhydrazinyl | |
| 1.142 | " | " | " | o-fluorophenyl-hydrazinyl | |
| 1.143 | " | " | " | o,p-difluorophenyl-hydrazinyl | |
| 1.144 | " | " | " | tert-butylhydrazinyl | |
| 1.145 | " | " | " | NH—N⌐O⌐=O | |
| 1.146 | S | " | " | phenyl-hydrazinyl | |
| 1.147 | " | " | " | o-fluorophenyl-hydrazinyl | |
| 1.148 | " | " | " | o,p-difluorophenyl-hydrazinyl | |
| 1.149 | " | " | " | tert-butylhydrazinyl | |
| 1.150 | " | " | " | NH—N⌐O⌐=O | |

TABLE 2

Compounds of formula Ib

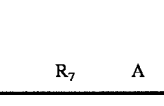

| Comp. No. | Y | R₆ | R₇ | A | m.p. [°C.]/ phys. data |
|---|---|---|---|---|---|
| 2.001 | O | CH₃ | H | [Val]—OH | 112–114° |
| 2.002 | " | " | " | [Ala]—OEt | [α]<sub>D</sub>−28.8° |
| 2.003 | " | " | " | [Gly]—OEt | |
| 2.004 | " | " | " | [Ile]—OMe | |
| 2.005 | " | " | " | [Leu]—OMe | |
| 2.006 | " | " | " | [Val]—OMe | |
| 2.007 | S | " | " | [Ala]—OEt | |
| 2.008 | " | " | " | [Ala]—OH | |
| 2.009 | " | " | CH₃ | [Ala]—OEt | |
| 2.010 | " | " | " | [Ala]—OH | |
| 2.011 | " | " | " | phenyl-hydrazinoyl | |
| 2.012 | " | " | " | dimethyl-hydrazinoyl | |
| 2.013 | " | " | H | dimethyl-hydrazinoyl | |
| 2.014 | " | " | CH₃ | tert-butyl-hydrazinoyl | |
| 2.015 | " | " | H | tert-butyl-hydrazinoyl | |
| 2.016 | O | " | " | tert-butyl-hydrazinoyl | |
| 2.017 | " | " | CH₃ | dimethyl-hydrazinoyl | |
| 2.018 | " | " | H | o-chloro-phenyl-hydrazinoyl | |
| 2.019 | " | " | " | p-fluoro-phenyl-hydrazinoyl | |
| 2.020 | " | —CH=CH—CH=CH— | | dimethyl-hydrazinoyl | |

Note: [α]<sub>D</sub> should be $[\alpha]_D$

TABLE 4

Compounds of formula VIa'

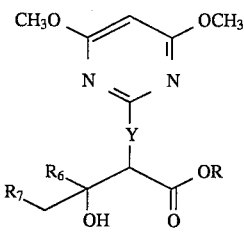

| Comp. No. | Y | $R_3$ | $R_7$ | R | mp [°C.]/Phys. Data |
|---|---|---|---|---|---|
| 4.001 | S | $CH_3$ | H | $CH_3$ | Resin |
| 4.002 | S | $C_2H_5$ | $CH_3$ | t-Butyl | |
| 4.003 | S | i-Propyl | H | t-Butyl | |
| 4.004 | S | n-Propyl | H | t-Butyl | |
| 4.005 | S | $-CH_2CH_2CH_2-$ | | $CH_2CH_3$ | Resin |
| 4.006 | S | $-CH_2CH_2CH_2CH_2-$ | | t-Butyl | |
| 4.007 | S | $CH_3$ | $CH_3$ | $CH_2CH=CH_2$ | $^1$H-NMR (CDCl$_3$): 1,32, d, CH$_3$; 1,72, m, CH$_2$; 3,92, s, OCH$_3$; 4,83, s; 5,76, s, CH. |
| 4.008 | S | $CH_3$ | H | t-Butyl | Resin |
| 4.009 | S | $CH_3$ | $CH_3$ | t-Butyl | $^1$H-NMR (CDCl$_3$): 1,33 + 1,38, 2s, CH$_3$; 3,94, s, OCH$_3$; 4,71 + 4,72, 2s, CH; 5,78, s, CH. |

TABLE 5

Compounds of formula VIIIa

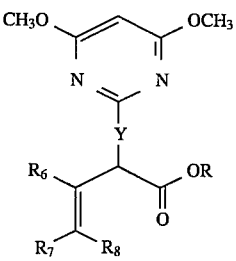

| Comp. No. | Y | $R_6$ | $R_7$ | $R_8$ | R | m.p. [°C.], phys. data |
|---|---|---|---|---|---|---|
| 5.001 | S | $CH_3$ | H | H | $C_2H_5$ | 50–52 |
| 5.002 | S | $CH_3$ | $CH_3$ | H | $C_2H_5$ | oil |
| 5.003 | S | $CH_3$ | $CH_3$ | $CH_3$ | tert-butyl | |
| 5.004 | S | $C_2H_5$ | $CH_3$ | H | tert-butyl | |
| 5.005 | S | $C_2H_5$ | H | H | $C_2H_5$ | oil |
| 5.006 | S | $C_2H_5$ | H | $CH_3$ | tert-butyl | |
| 5.007 | S | $-CH_2CH_2CH_2-$ | | H | tert-butyl | |
| 5.008 | S | $-CH_2CH_2CH_2CH_2-$ | | H | tert-butyl | |
| 5.009 | S | $CH_3$ | $CH_3$ | H | tert-butyl | oil |
| 5.010 | S | $C_2H_5$ | H | H | tert-butyl | oil |
| 5.011 | S | $CH_3$ | $CH_3$ | H | H | 116–123 (E/Z isomer 9:1) |
| 5.012 | S | $C_2H_5$ | H | H | H | oil |
| 5.013 | S | $CH_3$ | H | H | H | solid |
| 5.014 | S | $CH_3$ | $CH_3$ | $CH_3$ | H | |
| 5.015 | S | $C_2H_5$ | $CH_3$ | H | H | |
| 5.016 | S | $C_2H_5$ | H | $CH_3$ | H | |

TABLE 6

Compounds of formula Ia

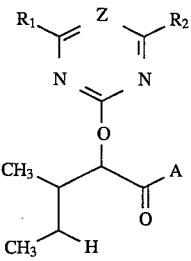

| Comp. No. | Z | $R_1$ | $R_2$ | A | m.p. [°C.] phys. data |
|---|---|---|---|---|---|
| 6.001 | N | $OCH_3$ | $OCH_3$ | [Ala]—OEt | |
| 6.002 | N | $OCH_3$ | $OCH_3$ | [Leu]—OEt | |
| 6.003 | N | $OCH_3$ | $OCH_3$ | [Asp]—(OEt)$_2$ | |
| 6.004 | CH | $CH_3$ | $CH_3$ | [Ala]—OMe | |
| 6.005 | CH | $CH_3$ | $CH_3$ | [Leu]—OMe | |
| 6.006 | CH | $CH_3$ | $CH_3$ | [Asp]—(OMe)$_2$ | |
| 6.007 | N | $OCH_3$ | $OCH_3$ | phenylhydrazinyl | |
| 6.008 | N | $OCH_3$ | $OCH_3$ | o-fluorophenyl-hydrazinyl | |
| 6.009 | N | $OCH_3$ | $OCH_3$ | o,p-difluorophenyl-hydrazinyl | |
| 6.010 | N | $OCH_3$ | $OCH_3$ | tert-butylhydrazinyl | |
| 6.011 | N | $OCH_3$ | $OCH_3$ | NH—N(cyclic group) | |
| 6.012 | CH | $CH_3$ | $CH_3$ | phenylhydrazinyl | |
| 6.013 | CH | $CH_3$ | $CH_3$ | o-fluorophenyl-hydrazinyl | |
| 6.014 | CH | $CH_3$ | $CH_3$ | o,p-difluorophenyl-hydrazinyl | |
| 6.015 | CH | $CH_3$ | $CH_3$ | tert-butylhydrazinyl | |

TABLE 6-continued

Compounds of formula Ia $$R_1\diagdown_{N}^{Z}\diagup R_2$$
(structure with central C bonded to N, N, O-CH(CH3)-CH(CH3)(H)-C(=O)-A) — Ia

| Comp. No. | Z | $R_1$ | $R_2$ | A | m.p. [°C.] phys. data |
|---|---|---|---|---|---|
| 6.016 | CH | $CH_3$ | $CH_3$ | NH—N(—CH2CH2—)C(=O) (succinimide-like ring with NH-N) | |
| 6.017 | CH | $OCH_3$ | $OCH_3$ | NH—N(—CH2CH2—)C(=O) | |
| 6.018 | CH | $CH_3$ | $OCH_3$ | NH—N(—CH2CH2—)C(=O) | |
| 6.019 | CH | $CH_3$ | $CH_3$ | NH—N(—CH2CH2—)C(=O) | |
| 6.020 | N | $OCH_3$ | $OCH_3$ | NH—N(—CH2CH2—)C(=O) | |

TABLE 7

Compounds of formula Ia $$CH_3O\diagdown\diagup OCH_3$$ 
(Ia)

(pyrimidine-type structure with N, N, Y, then CR3(CH3)(R5)-C(=O)-A)

| Comp. No. | Y | $R_3$ | $R_5$ | A | m.p. [°C.] phys. data |
|---|---|---|---|---|---|
| 7.001 | S | $CH_3$ | CN | [Ala]—OEt | |
| 7.002 | S | $CH_3$ | CN | [Leu]—OMe | |
| 7.003 | S | $C_2H_5$ | CN | [Ala]—OEt | |
| 7.004 | O | $CH_3$ | F | [Ala]—OEt | |
| 7.005 | O | $CH_3$ | F | [Leu]—OMe | |
| 7.006 | O | $CH_3$ | F | [Asp]—(OMe)$_2$ | |
| 7.007 | O | $CH_3$ | F | phenylhydrazinyl | |
| 7.008 | O | $CH_3$ | F | o-fluorophenyl-hydrazinyl | |
| 7.009 | O | $CH_3$ | F | o,p-difluoro-phenylhydrazinyl | |
| 7.010 | O | $CH_3$ | F | tert-butylhydrazinyl | |
| 7.011 | O | $CH_3$ | F | NH—N(—CH2CH2—)C(=O) | |
| 7.012 | O | $C_2H_5$ | F | [Ala]—OEt | |
| 7.013 | O | phenyl | F | [Ala]—OEt | |
| 7.014 | O | cyclohexyl | F | [Ala]—OEt | |
| 7.015 | O | cyclopentyl | F | [Ala]—OEt | |
| 7.016 | O | $CH_3$ | isopropoxy | [Ala]—OEt | |
| 7.017 | O | $CH_3$ | methoxy-ethoxy | [Ala]—OEt | |
| 7.018 | O | $CH_3$ | 2-propenyl-oxy | [Leu]—OMe | |
| 7.019 | O | $C_2H_5$ | 2-propynyl-oxy | [Ala]—OMe | |
| 7.020 | O | $C_2H_5$ | benzyloxy | [Ala]—OEt | |
| 7.021 | O | $CH_3$ | OMe | [Ala]—OMe | |
| 7.022 | O | $CH_3$ | OEt | [Ala]—OEt | |
| 7.023 | O | $C_2H_5$ | OMe | [Ala]—OMe | |
| 7.024 | O | $C_2H_5$ | OEt | [Ala]—OEt | |
| 7.025 | O | $CH_3$ | OMe | o-fluorophenyl-hydrazinoyl | |
| 7.026 | O | $C_2H_5$ | OMe | o-fluorophenyl-hydrazinoyl | |
| 7.027 | O | $CH_3$ | OMe | o-tert-butyl | |
| 7.028 | O | $CH_3$ | OMe | NH—N(—CH2CH2—)C(=O) | |
| 7.029 | O | $CH_3$ | OMe | [Leu]—OMe | |
| 7.030 | O | $CH_3$ | OMe | [Aspl]—(OMe)$_2$ | |
| 7.031 | S | $C_2H_5$ | CN | [Leu]—OMe | |
| 7.032 | S | $CH_3$ | F | [Ala]—OEt | |
| 7.033 | S | $CH_3$ | F | [Leu]—OMe | |
| 7.034 | S | $C_2H_5$ | F | [Ala]—OEt | |
| 7.035 | S | $C_2H_5$ | F | [Leul]—OMe | |

Biological Examples

Example B 1

Pre-emergence herbicidal action

Monocotyledonous and dicotyledonous test plants are sown in standard soil in plastic pots. Immediately after sowing, an aqueous suspension of the test compounds is applied by spraying at a rate of application corresponding to 2 kg of active ingredient/hectare (500 l water/ha). The test plants are then cultivated in a greenhouse under optimum conditions. After 3 weeks the test is evaluated in accordance with a scale of nine ratings (1=total damage, 9=no action). Ratings of from 1 to 4 (especially from 1 to 3) indicate good to very good herbicidal action.

The compounds of formula I described in Tables 1-2 and 6-7 exhibit strong herbicidal action in this test.

Examples of the good herbicidal action of the compounds of formula I described in Tables 1-2 of this Application are given in Table B1:

TABLE B1

| Comp. No. | Pre-emergence herbicidal action: | | | |
|---|---|---|---|---|
| | Avena | Setaria | Sinapis | Stellaria |
| 1.002 | 2 | 2 | 2 | 2 |
| 1.004 | 3 | 1 | 2 | 2 |
| 1.006 | 3 | 2 | 2 | 3 |
| 1.008 | 3 | 2 | 3 | 3 |
| 1.009 | 3 | 2 | 2 | 2 |
| 1.010 | 3 | 1 | 3 | 1 |
| 1.011 | 3 | 3 | 3 | 3 |
| 1.012 | 3 | 1 | 2 | 2 |
| 1.015 | 3 | 1 | 2 | 1 |
| 1.019 | 2 | 1 | 2 | 2 |
| 1.021 | 2 | 1 | 2 | 2 |
| 1.022 | 2 | 1 | 2 | 2 |
| 1.023 | 2 | 1 | 2 | 2 |
| 1.024 | 2 | 2 | 2 | 2 |
| 1.026 | 3 | 2 | 3 | 2 |
| 1.027 | 3 | 2 | 3 | 2 |
| 1.029 | 3 | 2 | 2 | 2 |
| 1.302 | 3 | 2 | 3 | 2 |
| 1.101 | 3 | 2 | 2 | 2 |

Example B2

Post-emergence herbicidal action (contact herbicide)

In a greenhouse, monocotyledonous and dicotyledonous test plants are raised in plastic pots containing standard soil and at the 4- to 6-leaf stage are sprayed with an aqueous suspension of the test compounds at a rate of application corresponding to 2 kg active ingredient/ha (500 l water/ha). The test plants are then grown on in the greenhouse under optimum conditions. After about 18 days the test is evaluated in accordance with a scale of nine ratings (1=total damage, 9=no action). Ratings of from 1 to 4 (especially from 1 to 3) indicate good to very good herbicidal action.

In this test too, the compounds of formula I described in Tables 1-2 and 6-7 exhibit very strong herbicidal action.

Examples of the good herbicidal action of the compounds of formula I described in Tables 1-2 and 6-7 of this Application are given in Table B2:

TABLE B2

| Comp. No. | Post-emergence herbicidal action: | | | |
|---|---|---|---|---|
| | Avena | Setaria | Sinapis | Stellaria |
| 1.002 | 2 | 3 | 2 | 3 |
| 1.010 | 3 | 3 | 2 | 2 |
| 1.011 | 3 | 3 | 3 | 3 |
| 1.012 | 3 | 3 | 2 | 3 |
| 1.015 | 3 | 3 | 2 | 3 |
| 1.019 | 3 | 3 | 3 | 3 |
| 1.029 | 3 | 3 | 3 | 3 |
| 1.101 | 2 | 4 | 1 | 1 |

Example B3

Herbicidal action in wild rice (paddy)

The test plant is sown on the surface of standard soil in plastic beakers and the beakers are then filled with water up to the surface of soil. 3 days later, the test plants are treated with an aqueous suspension of the test compounds at a rate of application corresponding to 2 kg active ingredient/ha (500 l water/ha). Immediately after application the water level is increased by 1 cm and the test plants are grown on in a greenhouse under optimum conditions. The test is evaluated 2 weeks after application. The compounds of formula I described in Tables 1-2 and 6-7 exhibit strong herbicidal action against the weeds in this test.

Formulation Examples for active ingredients of formula I (throughout, percentages are by weight)

| 1. Wettable powders | a) | b) | c) |
|---|---|---|---|
| a compound of Tables 1-2, 6-7 | 20% | 50% | 0.5% |
| sodium lignosulfonate | 5% | 5% | 5% |
| sodium laurylsulfate | 3% | — | — |
| sodium diisobutylnaphthalene-sulfonate | — | 6% | 6% |
| octylphenol polyethylene glycol ether (7-8 mols of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| 2. Emulsifiable concentrate | a) | b) |
|---|---|---|
| a compound of Tables 1-2, 6-7 | 10% | 1% |
| calcium dodecylbenzenesulfonate | 3% | 3% |
| octylphenol polyethylene glycol ether (4-5 mols of ethylene oxide) | 3% | 3% |
| castor oil polyethylene glycol ether (36 mols of ethylene oxide) | 4% | 4% |
| cyclohexanone | 30% | 10% |
| xylene mixture | 50% | 79% |

Emulsions of any required concentration can be obtained from such concentrates by dilution with water.

| 3. Dusts | a) | b) |
|---|---|---|
| a compound of Tables 1-2, 6-7 | 0.1% | 1% |
| talcum | 99.9% | — |
| kaolin | — | 99% |

Ready-for-use dusts are obtained by homogeneously mixing the carrier with the active ingredient.

| 4. Extruder granules | a) | b) |
|---|---|---|
| a compound of Tables 1-2, 6-7 | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is moistened with water. The mixture is extruded and then dried in a stream of air.

| 5. Coated granules | |
|---|---|
| a compound of Tables 1–2, 6–7 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 6. Suspension concentrate | a) | b) |
|---|---|---|
| a compound of Tables 1–2, 6–7 | 5% | 40% |
| ethylene glycol | 10% | 10% |
| nonylphenol polyethylene glycol ether (15 mols of ethylene oxide) | 1% | 6% |
| sodium lignosulfonate | 5% | 10% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 77% | 32% |

The finely ground active ingredient is intimately mixed with the adjuvants, giving a suspension concentrate from which suspensions of any desired concentration can be obtained by dilution with water.

| 7. Salt solution | |
|---|---|
| a compound of Tables 1–2, 6–7 | 5% |
| isopropylamine | 1% |
| octylphenol polyethylene glycol ether (78 mols of ethylene oxide) | 91% |

The compounds of formula I are used in unmodified form or, preferably, in the form of compositions together with the adjuvants customarily employed in formulation technology and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, scattering or pouring, are chosen in accordance with the intended objectives and the prevailing circumstances.

What is claimed is:

1. A pyrimidinyloxy- or triazinyloxy- or pyrimidinylthio- or triazinylthio-propionic acid derivative of formula I

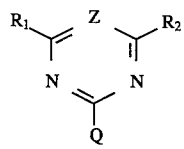

wherein

Q is

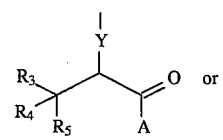

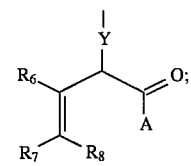

A is a group

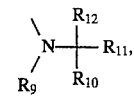

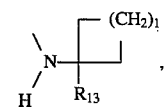

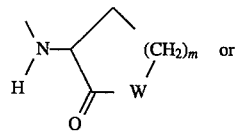

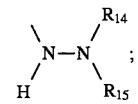

Y is oxygen or sulfur;

Z is nitrogen;

$R_1$ is methyl, ethyl, cyclopropyl, methoxy, ethoxy, difluoromethoxy, methylthio, ethylthio, methylamino, ethylamino, dimethylamino or diethylamino;

$R_2$ is methyl, fluorine, chlorine, methoxy, ethoxy or difluoromethoxy;

$R_3$ is hydrogen, $C_{1-6}$alkyl, $C_{3-6}$cycloalkyl, $C_{1-6}$alkyl mono-substituted by chlorine or mono- to hexa-substituted by fluorine; phenyl, thienyl, or phenyl or thienyl mono- or di-substituted by fluorine, chlorine, methyl or by methoxy;

$R_4$ is hydrogen, $C_{1-3}$alkyl or, together with $R_3$, $-(CH_2)_n-$;

$R_5$ is hydrogen, methyl, fluorine, chlorine, bromine, $C_{1-6}$alkoxy, $C_{3-6}$alkenyloxy, $C_{3-6}$alkynyloxy, $C_{3-4}$cycloalkyl-$C_{1-2}$alkoxy, $C_{4-6}$cycloalkoxy, $C_{1-4}$alkoxy mono-substituted by cyano, phenyl, $C_{1-2}$alkoxy or chlorine or mono- to hexa-substituted by fluorine; $C_{1-6}$alkylthio or cyano;

$R_6$ is hydrogen, $C_{1-6}$alkyl, phenyl or, together with $R_7$, $-(CH_2)_p-$, $-CH=CH-CH=CH-$, $-N=CH-CH=CH-$ or $-S-CH=CH-$;

$R_7$ is hydrogen or methyl;

$R_8$ is hydrogen or methyl:

$R_9$ is hydrogen, methyl or, together with $R_{11}$, $-(CH_2)_q-$, $-CH_2CH(OH)CH_2-$, $-CH_2SCH_2-$ or $-CH_2CH_2SCH_2-$;

$R_{10}$ and $R_{13}$ are each independently of the other hydroxymethyl, formyl, cyano, phosphono, phosphino, methylphosphino or a group COX, R₁₁ is hydrogen, C₁₋₄alkyl, trifluoromethyl, or C₁₋₄alkyl substituted by hydroxy, C₁₋₄alkoxy, mercapto, C₁₋₄alkylmerapto, vinyl, phenyl, 4-hydroxyphenyl, 4-imidazolyl, 3-indolyl, carboxy, C₁₋₄alkoxycarbonyl, 2-propenyloxycarbonyl, cyano, carbamoyl, methylphosphino or by methylsulfoximino; ethylnyl, vinyl, phenyl, or vinyl or phenyl substituted by chlorine, methyl or by methoxy;

R₁₂ is hydrogen or methyl;

R₁₄ is hydrogen or methyl;

R₁₅ is hydrogen, C₁₋₆alkyl, phenyl, or phenyl mono- or di-substituted by fluorine, chlorine, bromine, iodine, C₁₋₄alkyl, trifluoromethyl, C₁₋₃alkoxy, difluoroalkoxy, cyano, nitro or by C₁₋₄alkoxycarbonyl; pyridyl, or pyridyl mono- or di-substituted by fluorine, chlorine, methyl, methoxy or by trifluoromethyl; or, R₁₄ and R₁₅ together are —C(O)—CH₂—CH₂—, —(CH₂)₄— or —(CH₂)₂O(CH₂)— and form a ring with the nitrogen atom to which they are linked;

l is 0, 1, 2 or 3;

m is 0, 1, 2 or 3;

n is 2, 3, 4 or 5;

p is 3 or 4;

q is 2 or 3;

W is oxygen, sulfur, NH or —NH—O—;

X is hydroxy, C₁₋₄alkoxy, C₃₋₄alkenyloxy, benzyloxy, amino, C₁₋₄alkylamino, C₂₋₄-dialkylamino or a group

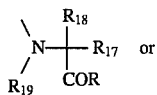 (X₁)

or

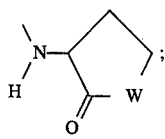 (X₂)

R₁₆ is hydroxy, C₁₋₄alkoxy, 2-propenyloxy, benzyloxy, amino or a further amino acid group (X₁);

R₁₇ is hydrogen, C₁₋₄alkyl or benzyl;

R₁₈ is hydrogen or methyl;

R₁₉ is hydrogen or, together with R₁₇, —(CH₂)₃—; or a salt of such a compound of formula I having a free carboxy group; with the proviso that Y is sulfur when R₁ and R₂ are methoxy, Q is Q₁, R₃ and R₄ are methyl, R₅ is hydrogen, A the group A₄, and R₁₄ and R₁₅ are simultaneously either hydrogen or methyl.

2. A compound of formula I according to claim 1 wherein

R₃ is hydrogen, C₁₋₆alkyl, C₃₋₆cycloalkyl, C₁₋₆alkyl monosubstituted by chlorine or mono- to hexa-substituted by fluorine; phenyl, thienyl, or phenyl mono- or di-substituted by fluorine, chlorine, methyl or by methoxy;

R₄ is hydrogen, methyl or, together with R₃, —(CH₂)ₙ—;

R₅ is hydrogen, methyl, fluorine, chlorine, bromine, C₁₋₆alkoxy, C₃₋₆alkenyloxy, C₃₋₆alkynyloxy, C₃₋₄cycloalkyl-C₁₋₂alkoxy, C₄₋₆cycloalkoxy, C₁₋₄alkoxy mono-substituted by cyano, C₁₋₂alkoxy or chlorine or mono- to hexa-substituted by fluorine; C₁₋₆alkylthio or cyano, and R₆ is hydrogen, C₁₋₄alkyl, phenyl or, together with R₇, —(CH₂)ₚ—, —CH=CH—CH=CH—, —N=CH—CH=CH— or —S—CH=CH—.

3. A compound of formula I according to claim 1 wherein Q is a group

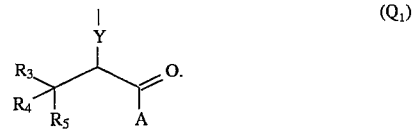 (Q₁)

4. A compound of formula I according to claim 1 wherein A is a group

 (A₁)

or

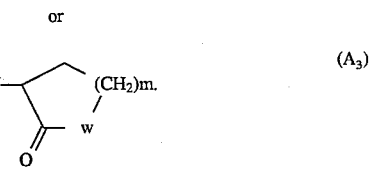 (A₃)

5. A compound of formula I according to claim 1 wherein A is a group

 (A₄)

6. A compound of formula I according to claim 3 wherein R₃ is C₁₋₃alkyl or phenyl, R₄ is methyl or, together with R₃, —(CH₂)₄—, and R₅ is hydrogen, fluorine, methyl, cyano or C₁₋₄-alkoxy.

7. A compound of formula I according to claim 4 wherein

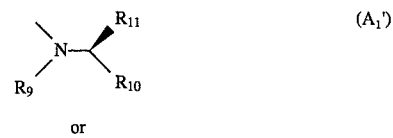 (A₁')

or

 (A₃')

wherein R₉ is hydrogen or, together with R₁₁, —(CH₂)₃—; R₁₀ is a group COX wherein X is as defined for formula I in claim 1, R₁₁ is hydrogen or C₁₋₄alkyl, and W is oxygen or sulfur.

8. A compound of formula I according to claim 5 wherein R₁₄ is hydrogen or methyl and R₁₅ is C₁₋₄alkyl, phenyl, or phenyl mono- or di-substituted by fluorine, chlorine, methyl, trifluoromethyl, methoxy or by nitro; pyridyl or pyrazinyl; or pyridyl or pyrazinyl mono- or di-substituted by fluorine, chlorine, methyl or by trifluoromethyl;

or R₁₄ and R₁₅ together are —C(O)—CH₂—CH₂—, —(CH₂)₄— or —(CH₂)₄— or —(CH₂)₂O(CH₂)₂— and form a ring with the nitrogen atom to which they are linked.

9. A compound of formula I according to claim 8 wherein R₁₄ is hydrogen, and

R₁₅ is tert-butyl, phenyl, or phenyl mono- or di-substituted by fluorine, chlorine, methyl, trifluoromethyl, methoxy or by nitro; pyridyl or pyrazinyl; or pyridyl or pyrazinyl mono- or di-substituted by fluorine, chlorine, methyl or by trifluoromethyl; or $R_{14}$ and $R_{15}$ together are —C(O)—CH$_2$—CH$_2$—, —(CH$_2$)$_4$— or —(CH$_2$)$_2$O(CH$_2$)$_2$— and form a ring with the nitrogen atom to which they are linked.

10. A compound of formula I according to claim 1 wherein Y is oxygen.

11. A compound of formula I according to claim 1 wherein $R_1$ is methyl, dimethylamino or methoxy and $R_2$ is methyl, methoxy, ethoxy or difluoromethoxy.

12. A compound of formula I according to claim 1 wherein $R_1$ and $R_2$ are methoxy.

13. A herbicidal and plant growth regulating composition comprising one or more compounds of formula I according to claim 1 and a carrier.

14. A composition according to claim 13 comprising from 0.001% to 95% by weight of a compound of formula I and a carrier.

15. A method of controlling undesirable plant growth, which comprises applying an effective amount of a compound of formula I according to claim 1, or of a composition comprising such a compound, to the plant or to the locus thereof and a carrier.

16. A method according to claim 15 for the selective pre- or post-emergence control of weeds in crops of useful plants.

17. A method of regulating plant growth, which comprises applying an effective amount of a compound of formula I according to claim 1, or of a composition comprising such a compound, to the plant or to the locus thereof and a carrier.

18. A method according to claim 17, wherein the effective amount is from 0.001 to 2 kg per hectare.

* * * * *